United States Patent
Sonis

(10) Patent No.: US 7,297,123 B2
(45) Date of Patent: Nov. 20, 2007

(54) METHOD AND APPARATUS FOR ACCESSING ORAL MUCOSITIS

(75) Inventor: Stephen T. Sonis, Wayland, MA (US)

(73) Assignee: Nova Technology Corporation, Portsmouth, NH (US)

( * ) Notice: Subject to any disclaimer, the term of this patent is extended or adjusted under 35 U.S.C. 154(b) by 239 days.

(21) Appl. No.: 10/907,844

(22) Filed: Apr. 18, 2005

(65) Prior Publication Data

US 2005/0234365 A1 Oct. 20, 2005

Related U.S. Application Data

(60) Provisional application No. 60/563,331, filed on Apr. 19, 2004.

(51) Int. Cl.
*A61B 5/103* (2006.01)
*A61B 5/05* (2006.01)

(52) U.S. Cl. ........... 600/590; 600/587; 600/547

(58) Field of Classification Search ........... 600/590, 600/587, 547

See application file for complete search history.

(56) References Cited

U.S. PATENT DOCUMENTS

| 5,353,802 | A | 10/1994 | Ollmar | |
|---|---|---|---|---|
| 2005/0119537 | A1* | 6/2005 | Campbell et al. | 600/306 |
| 2006/0116587 | A1* | 6/2006 | Ling et al. | 600/485 |

\* cited by examiner

*Primary Examiner*—Max F. Hindenburg
*Assistant Examiner*—H. Q. Nguyen
(74) *Attorney, Agent, or Firm*—George A. Herbster

(57) ABSTRACT

Overall and constituent oral mucositis assessment scale scores are generated by the use of a probe to obtain moisture measurements at a particular site. A control collects data samples. A converter produces a value for the oral mucositis assessment scale (OMAS) in response to the collected data (DPM) in accordance with a correlation defined by:

$$OMAS = \frac{DPM - DPM_o}{K(I)}.$$

16 Claims, 6 Drawing Sheets

METHOD AND APPARATUS FOR ACCESSING ORAL MUCOSITIS

FIELD OF THE INVENTION

This invention is directed to the assessment of oral mucositis. More specifically, this invention is directed to a method and apparatus for simplifying the assessment of patients afflicted with oral mucositis.

DESCRIPTION OF RELATED ART

Oral mucositis is a frequent complication of chemotherapy and radiotherapy regimens, hematopoietic stem-cell transplantation and various diseases. Oral mucositis is especially severe for patients who are undergoing stem-cell transplantation because this regimen involves the use of high dose myeloablative chemotherapy for conditioning. During the stem-cell transplantation regimen, oral mucositis can become so severe that patients require parenteral narcotics for relief of pain. In the presence of neutropenia, severe mucositis may predispose patients to septicemia.

Once the complications of oral mucositis were known, various methods were developed for assessing the severity of oral mucositis. Initial diagnoses were qualitative and led to ad hoc treatments. Most prior diagnostic tools and protocols were toxicity scales that emphasized the functional disability engendered by mucositis. However, these tools and protocols neglect anatomic characteristics. The scoring of these various scales was subjective and heavily influenced by the severity of pain experienced by the patient and the use of analgesics that can impart a downward bias to the scores off patients with anatomically severe oral mucositis. The lack of an objective, reliable and valid scale for measuring the extent of oral mucositis was an impediment to research in this area.

More recently a medical team developed a new scoring system for evaluating the anatomic extent and severity of oral mucositis. This study generated an Oral Mucositis Assessment Scale (OMAS) as a tool for assessing the severity of oral mucositis. In accordance with this scale, a physician evaluates multiple regions of the oral cavity for erythema and the presence and size of ulcerations or pseudo membranous. For example, erythema is evaluated as being "none", "mild/moderate" or "severe." The presence and size of ulcerations or pseudo membranes are evaluated as being "none", "<1 $cm^2$", "1 to 3 $cm^2$", or ">3 $cm^2$." In patients receiving ablative chemotherapy and bone marrow transplantation, there is a significant correlation between OMAS scores and oral pain, difficulty swallowing and inability to eat. With the exception of fever, there is a close correlation between peak OMAS scores and selected clinical and economic outcomes in blood and marrow transplantation.

Although OMAS scoring provides at least a pseudo-quantitative approach, scoring a particular patient still requires sophisticated knowledge and the implementation of somewhat subjective evaluation techniques. There is such a strong requirement for training and because the categorization of erythema and the presence and size of ulcerations or pseudo membranes introduce some subjective analysis in assigning a particular rating for scoring. Moreover, such approaches are dependent on the medical personnel who have the requisite training. That is, two physicians examining the same patient are prone to rate the same patient with slightly different scores.

What is needed is an objective repeatable test that will provide an OMAS score as an accurate assessment of oral mucositis. Moreover, what is needed is a method and apparatus that allows support staff to do the diagnosis with a measure of repeatability of OMAS scores with patients of similar levels of oral mucositis.

SUMMARY

Therefore it is an object of this invention to provide a method and apparatus for enabling the assessment of oral mucositis.

In accordance with this invention a value or an oral mucositis assessment scale at a site in a patient is obtained by acquiring data samples that represent the moisture content at the site. The acquired data samples are then converted to an oral mucositis assessment scale reading for display.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
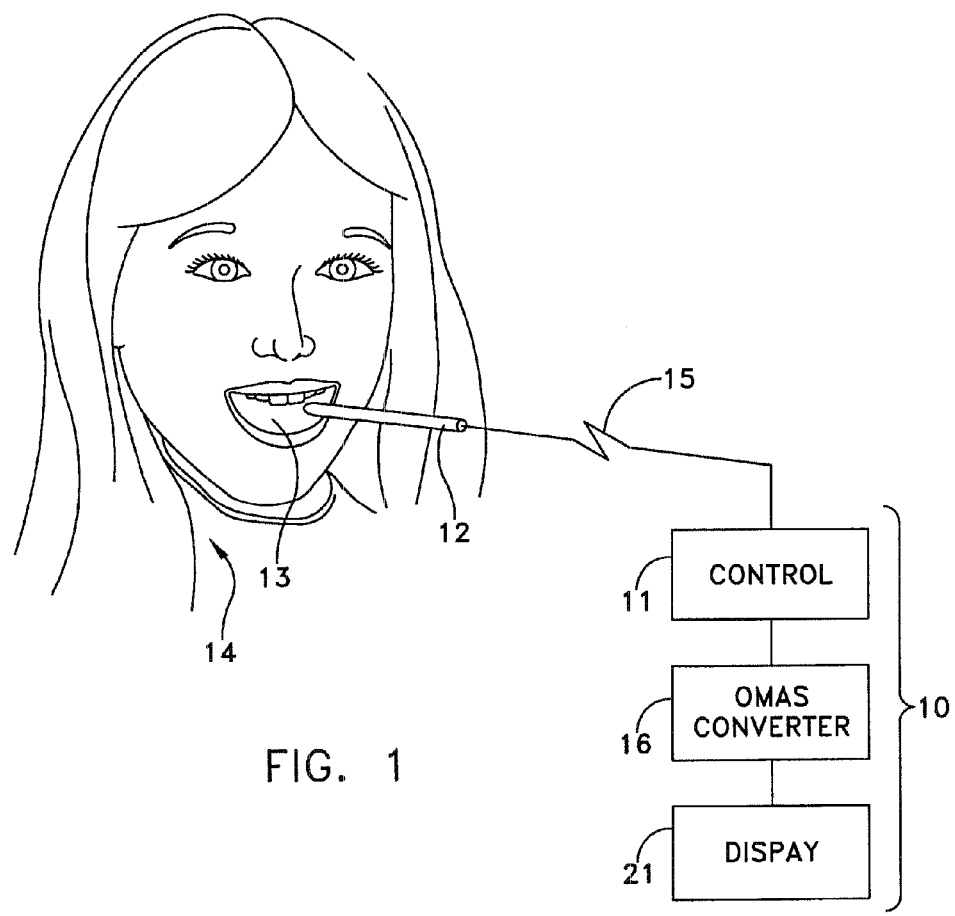
FIG. 1 depicts the apparatus for obtaining measurements in the oral cavity in accordance with this invention.

FIG. 1 depicts apparatus 10 for obtaining OMAS scores by means of the measurement of surface moisture. The apparatus 10 includes a DPM (Dermal Phase Meter) control 11 with a probe 12 for insertion in the mouth 13 of a patient 14. The DPM control 11 and probe 12 can comprise a dermatological instrument, such as a NOVA DPM 9020/Petite Dermal Phase Meter sold by Nova Technology Corporation, or any equivalent instrument. The Dermal Phase Meter control 11, probe 12 and interconnecting cable 15 cooperate to make measurements of moisture levels by contacting a sensor in the probe 12 with the skin or tissue. Specifically, the DPM control 11 and probe 12 take successive impedance measurements of the tissue in contact with the probe to obtain a capacitance value that correlates with a biophysical property of the skin, such as moisture level. Typically such Dermal Phase Meters have been used to make measurements of the capacitive reactance of skin, such as the skin on hands and other external surfaces of the body to provide evaluations of other processes and protocols, such as burn therapy.

Figure 2:
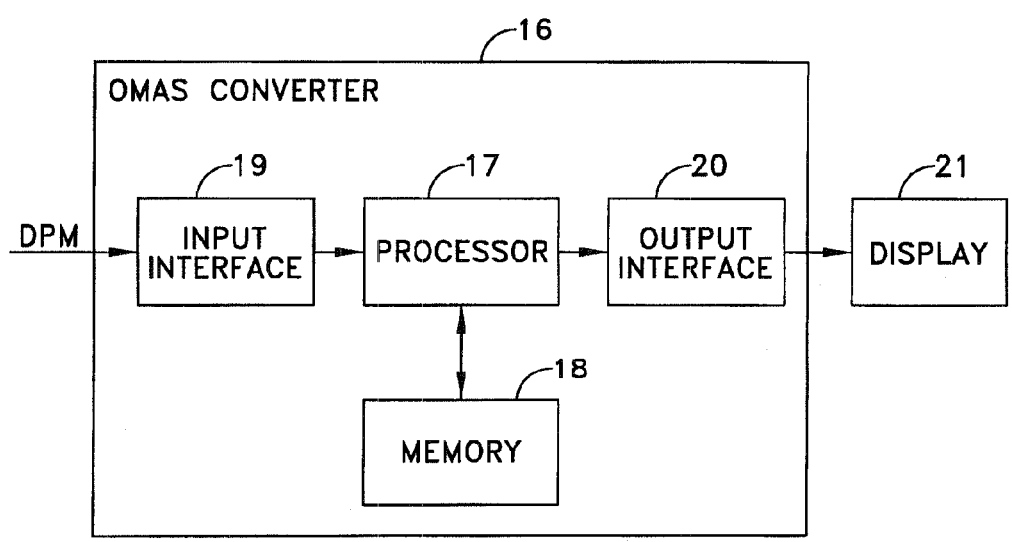
FIG. 2 is a block diagram of one embodiment of an OMAS converter as shown in FIG. 1.

In accordance with this invention, the output of the DPM control 11 transfers to an OMAS converter 16. An example of an OMAS converter 16 is shown in FIG. 2 as including a processor 17 with a memory 18. The processor 17 and memory 18 interact to receive DPM signals from the DPM control 11 through an input interface 19. An output interface 20 transfers signals to an output device, such as an external display 21 also shown in FIG. 1. As will be apparent, the OMAS converter 16 and display 21 could be implemented in a personal computer or other similar device that has the capacity for receiving the DPM signal, for performing the necessary data storage and analysis as will be described, and for providing an OMAS value.

Figure 3:
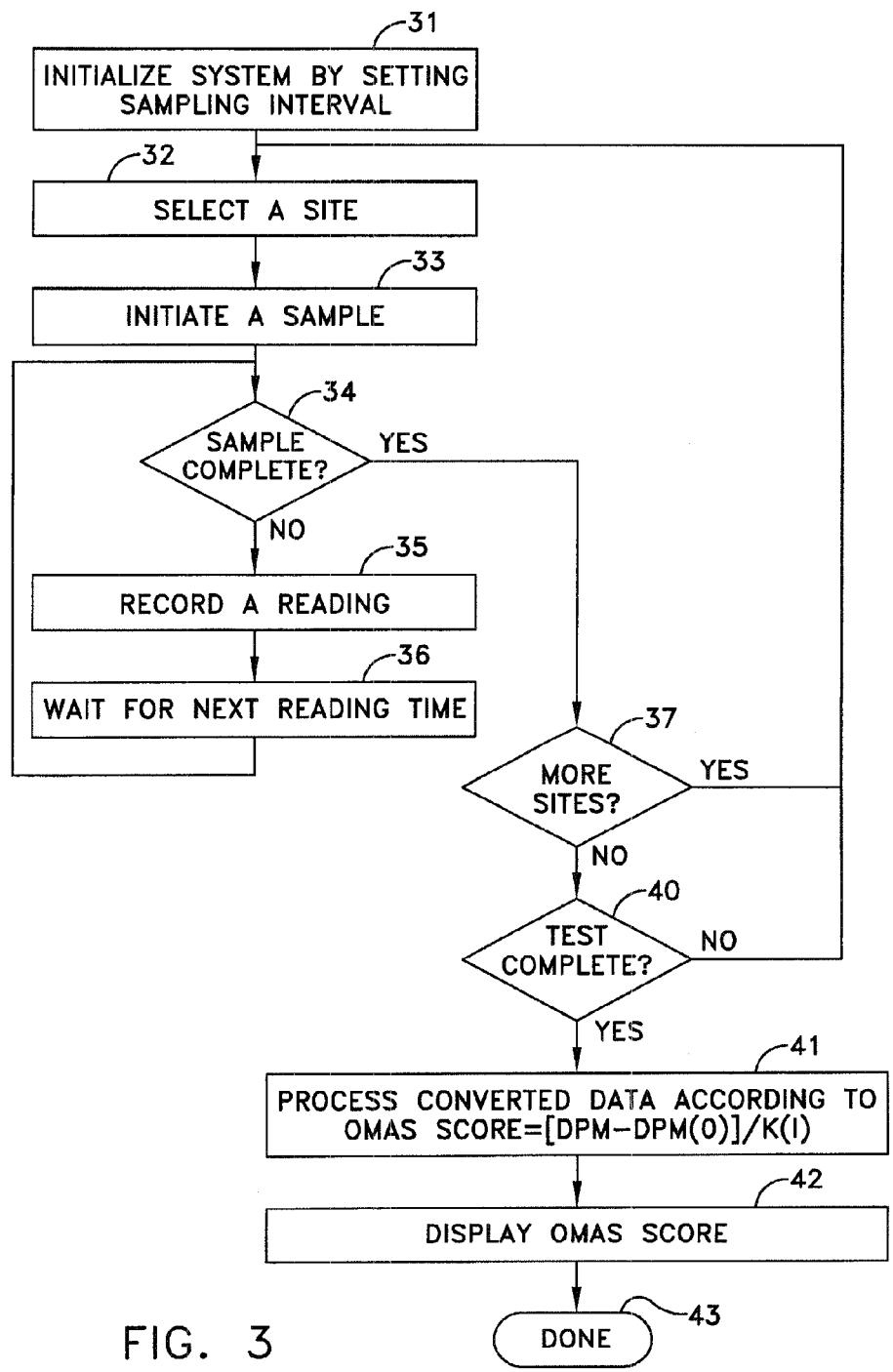
FIG. 3 is a flow diagram of the procedures used to process the data.

FIG. 3 depicts one procedure for implementing this invention as can be performed in a computer-based OMAS converter 16. Before discussing this procedure, it will be helpful to understand variations in the protocol for making these measurements and some basic operational characteristics of a Dermal Phase Meter. A Dermal Phase Meter, such as the DPM-9020 Dermal Phase Meter, generates a series of discrete readings at a frequency generally set by the manufacturer, but, in some embodiments, by the user. The rate at which such readings are taken is a reading rate and a reading time represents the time between successive readings. A sample comprises a set of readings. The set can be delimited by time or reading values. For the assessment of this invention, it is assumed that time will delimit the sample. In one assessment protocol the sample time begins shortly after the probe contacts the tissue at a site and terminates about ten seconds later.

An assessment may involve taking samples from multiple sites within the mouth, it may involve taking multiple samples from a single site in the mouth separated by some period of time, usually minutes. An assessment may also involve taking successive sets of multiple samples from multiple sites with readings for a first site in a set starting some time interval after the readings for a prior set have been completed.

The process shown in FIG. 3 for obtaining OMAS scores begins by initializing the system in step 31. In the particularly disclosed implementation of FIG. 3, the person running the system 10 sets sample time. That is, the person will identify the time during which readings are taken. Step 31 would also include setting other variables, such as the reading time, if such initialization were necessary.

Step 32 selects a site for testing. This provides the operator with the possibility of taking readings from a single or multiple sites. Step 33 initiates the readings for the sample once the probe 12 is properly located at a site with a patient's mouth.

Step 34 is a loop control for receiving and recording data readings from the DPM control 11 in FIG. 1. Initially step 34 transfers control to step 35 that records a data reading usually in a time-stamped format. Step 36 then establishes a wait interval corresponding to the reading time. This loop continues until the test sample has been completed as defined in step 31 whereupon control transfers to step 37.

Step 37 represents a step whereby the person conducting the assessment determines whether additional sites are to be sampled. If more sites are to be sampled, control transfers back to step 32 to perform the selection by moving the probe 12 to another site. Thus, the loop comprising steps 32 through 37 could be used to take a single sample from multiple sites, for example.

When all the sites have been sampled, step 37 transfers control to step 40 that represents another control point for the person administering the diagnoses. A test could be considered complete if all the sites have been measured one time. If the test is to involve multiple samples from multiple sites, step 40 transfers control back to step 32 to produce another set of samples. Although not shown, it will be apparent that step 40 could include some time interval or delay or other parameter to control the circumstances under what that control would transfer.

When the test is complete, step 40 transfers control to step 41 that converts this sampling to the OMAS score and displays the OMAS score at step 42, for example at the display 21 in FIGS. 1 and 2. Then step 43 terminates the process of FIG. 3.

Figure 4:
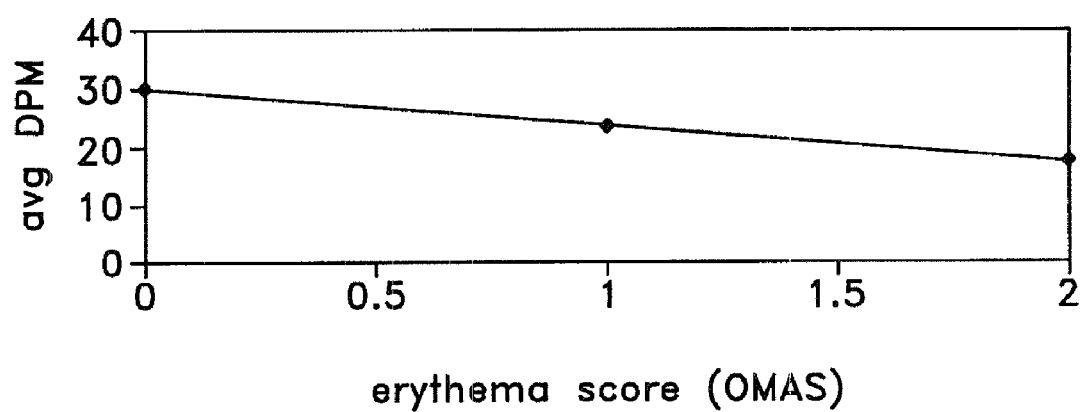
FIGS. 4 through 6 depict the relationship between various measurements and the OMAS scores.
Figure 5:
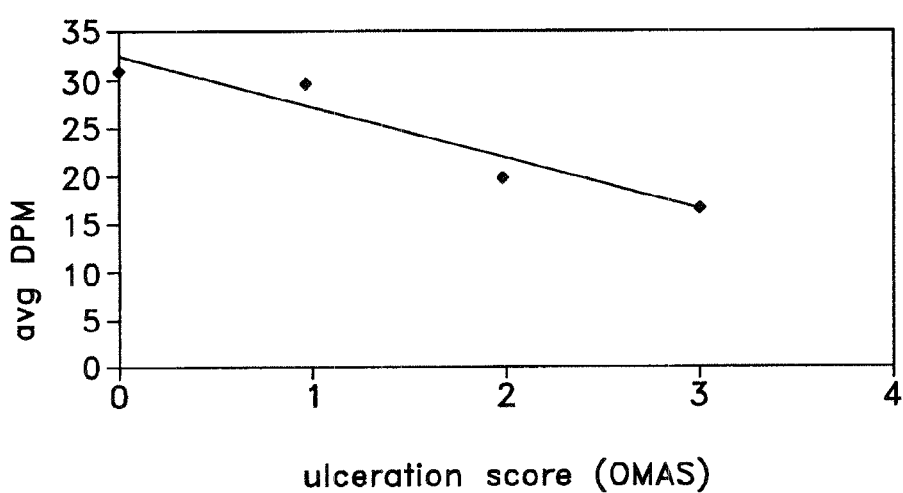
Figure 6:
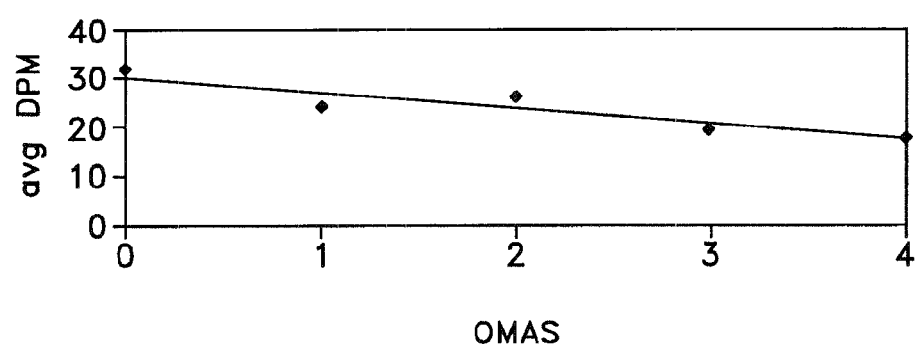

As previously indicated, an overall OMAS score has two constituents; namely (1) the contribution to the OMAS score of erythema and (2) the contribution to the OMAS score of ulceration. FIG. 4 depicts a relationship between the average DPM readings at different sites for a set of samples with respect to erythema. FIG. 5 depicts a relationship between the average DPM rating and ulceration scores; FIG. 6 depicts a relationship between average DPM readings and overall OMAS scores. In each of FIGS. 4 through 6 this relationship is linear. The slope of each of these graphs then represents the corresponding K(I) constant for that particular relationship.

Each analysis shown in FIGS. 4 through 6 exhibits a strong correlation between average DPM readings and total and constituent OMAS scores. Letting DPM represent average DPM readings, $DPM_0$ represent the DPM ready for a zero OMAS score and OMAS represent the OMAS score, each of FIGS. 4 through 6 define a general correlation of:

$$DPM = K(OMAS + DPM_0)$$

Solving the OMAS yields:

$$OMAS = \frac{DPM - DPM_0}{K(I)}$$

As will be apparent K(I) will vary with each analysis. With reference to FIGS. 4 through 6, K(I) will be a negative number. For specifically K(erythema)=−6; K(ulceration)=−5; and K(OMAS)=−3.

Referring again to FIG. 3, step 41 selects the appropriate value of K(I) to convert the data into a desired one of the constituent or overall OMAS score. Such a selection can be programmed into the converter.

It will now be apparent that the apparatus in FIGS. 1 and 2 combined with the processing according to FIG. 3, or equivalent apparatus and programming, produces an apparatus and protocol that provides objective OMAS scores based upon simply administered tissue measurements readily taught to nurses and other non-physician staff. Consequently it is possible to train medical staff to perform this diagnosis. Further, the diagnosis should be more consistent with respect to tests conducted by different untrained personnel. It will also be apparent that components of the specific structures and procedures disclosed in FIGS. 1 through 3 can be modified to facilitate use of the structure or operation of the structure. It is the intent of the appended claims to cover all such variations and modifications as come within the true spirit and scope of this invention.

What is claimed is:

1. Apparatus for providing a value of an oral mucositis assessment scale at an oral site comprising:
   A) measurement means for generating measured tissue moisture readings for the site,
   B) acquisition means for acquiring data samples of the measured tissue moisture readings for the site, and
   C) conversion means for converting the collected data samples to an oral mucositis assessment scale score.

2. Apparatus as recited in claim 1 wherein said measurement means comprises a dermal phase meter means for generating successive impedance measurements at the site as the tissue moisture readings.

3. Apparatus as recited in claim 1 wherein said measurement means comprises a dermal phase meter means for making successive impedance measurements at a plurality of sites as the tissue moisture readings.

4. Apparatus for providing a value of an oral mucositis assessment scale at an oral site comprising:
   A) measurement means for generating measured tissue moisture readings for the oral site,
   B) acquisition means for acquiring data samples of the measured tissue moisture readings for the site, and
   C) conversion means for converting the collected data samples to an oral mucositis assessment scale score wherein said conversion means includes means for generating an average of the samples, DPM, and means for generating the oral mucositis assessment scale score, OMAS, according to OMAS=(DPM-DPM0)/K(I) where K(I) is a constant and DPM0 is the value of DPM for a zero OMAS score.

5. Apparatus as recited in claim 4 wherein said conversion means includes means for storing values of K(I) for different analyses.

6. Apparatus as recited in claim 5 wherein the oral mucositis assessment scale score includes erythema and ulceration constituents and said conversion means stores values of K for erythema, ulceration and OMAS.

7. Apparatus as recited in claim 4 wherein said measurement means comprises a dermal phase meter means for making successive impedance measurements at the site.

8. Apparatus as recited in claim 7 wherein said measurement means generates readings at a given rate and said acquisition means includes means for selecting a group of readings as a data sample.

9. A method for providing a value of an oral mucositis assessment scale at an oral site comprising:
   A) generating measured tissue moisture readings for the site,
   B) acquiring data samples of the measured tissue moisture readings at the site, and
   C) converting the collected data samples to an oral mucositis assessment scale score.

10. A method as recited in claim 9 wherein said generation includes making successive impedance measurement readings at the site.

11. A method as recited in claim 9 wherein said generation includes making successive impedance measurements readings at a plurality of sites.

12. A method as recited in claim 9 wherein conversion includes generating an average of the samples, DPM, and generating the oral mucositis assessment scale, OMAS, according to OMAS=(DPM-DPM0)/K(I) where K(I) is a constant and DPM0 is the value of DPM for a zero OMAS score.

13. A method as recited in claim 12 wherein different values of K(I) are stored for different analyses.

14. A method as recited in claim 13 wherein the oral mucositis assessment scale score includes erythema and ulceration constituents and the stored values for K(I) are values for erythema, ulceration and OMAS.

15. A method as recited in claim 14 wherein said generation comprises making successive impedance measurements at the site.

16. A method as recited in claim 15 wherein said generation generates readings at a given rate of acquisition and selects a group of readings as a data sample.

\* \* \* \* \*